United States Patent [19]

Khau et al.

[11] Patent Number: 5,986,106
[45] Date of Patent: *Nov. 16, 1999

[54] PROCESS FOR PREPARING 4-SUBSTITUTED-1H-INDOLE-3-GLYOXAMIDES

[75] Inventors: Vien Van Khau, Carmel; Michael John Martinelli, Zionsville; Joseph Matthew Pawlak, Indianapolis, all of Ind.

[73] Assignee: Eli Lilly and Company, Indianapolis, Ind.

[*] Notice: This patent issued on a continued prosecution application filed under 37 CFR 1.53(d), and is subject to the twenty year patent term provisions of 35 U.S.C. 154(a)(2).

[21] Appl. No.: 09/105,381

[22] Filed: Jun. 26, 1998

Related U.S. Application Data

[60] Provisional application No. 60/050,877, Jun. 26, 1997, and provisional application No. 60/050,891, Jun. 26, 1997.

[51] Int. Cl.$^6$ .................................................. C07D 209/12
[52] U.S. Cl. .......................... 548/493; 548/486; 548/508; 548/469
[58] Field of Search .............................................. 548/493

[56] References Cited

U.S. PATENT DOCUMENTS 5,654,326   8/1997   Bach et al. ............................... 514/419

FOREIGN PATENT DOCUMENTS 21 45 573A    3/1973   Germany.
1 409 114    10/1975   Germany.
WO 96/15791   5/1996   WIPO.

OTHER PUBLICATIONS

V. I. Shvedov, et al., Pharm. Chem., 14:11, pp. 794–798, (1980).
C. Dagher, et al., J. Heterocycl. Chem., 19:3, pp. 645–647, (1982).
E. M. M. Van Den Berg, et al., Rec. Trav. Chim. Pays–Bas, 109:4, pp. 287–297, (1990).
V. I. Terenin, et al., Chem. Heterocycl. Compd., 26:9, pp. 1016–1022, (1990).
R. Brenneisen, et al., Arch. Pharm., 321, pp. 487–489, (1988).
D. B. Repke, et al., J. Heterocycl. Chem., 18, pp. 175–179, (1981).
F. Troxler, et al., Helv. Chim. Acta., 42:VI, pp. 2073–2103, (1959).
S. Torii, et al., Chem. Lett., 12, pp. 1603–1604, (1980).
H. Stetter, E. Siehnhold, Chem. Ber., 88, pp. 271–274, (1955).
W. A. Remers, M. J. Weiss, J. Amer. Chem. Soc., 87, pp. 5263–5264, (1965).
Patent Abstracts of Japan, 004:186, Feb. 10, 1980.
H. Iida, et al., Tetrahedron Lett., 23:35, pp. 3591–3594, (1982).
N. De Kimpe, et al., Synthesis, 2, pp. 188–190, (1987).

M. T. Reetz, et al., Angew Chem. Int. Ed. Eng.,18, p. 72, (1979).
M. W. Rathke, et al., J. Am. Chem. Soc., 93:9, pp. 2318–2320, (1971).
M. Hirama, et al., Tetrahedron Lett., 27:43, pp. 5281–5284, (1986).
D. F. Taber, et al., J. Am. Chem. Soc., 109:24, pp. 7488–7494, (1987).
P. T. Haken, Chemistry and Industry, p. 325, (Apr. 7, 1973).
R. J. Cregge, et al., Tetrahedron Lett., 26, pp. 2425–2428. (1973).
E. D. Edstrom, Synlett, Jan. 1995, pp. 49–50.
E. D. Edstrom, et al., Tetrahedron Lett., 36:39, pp. 7035–7038, (1995).
M. Matsumoto, et al., Heterocycles, 24:9, pp. 2611–2618, (1986).
H. Ishibashi, et al., Tetrahedron Lett., 34:3, pp. 489–492, (1993).
F. M. Hershenson, J. Org. Chem., 40:9, pp. 1260–1264, (1975).
M. Sainsbury, et al., Tetrahedron Lett., 49:10, pp.2065–2076, (1993).
M. Matsumoto, et al., Heterocycles, 23:1, pp. 165–170, (1985).
M. Matsumoto, et al., Heterocycles, 22:10, pp. 2313–2316, (1984).
J. Rebek, Jr., et al., J. Org. Chem., 49:26, pp. 5164–5174, (1984).
H. Stetter et al., Institute of Organic Chemistry of the Technical University of Aachen, Mar. 10, 1962.
J. M. Pawlak, et al., J. Org. Chem., 61:25, pp. 9055–9059, (1996).
D. R. Hutchison, et al., Tetrahedron Lett., 37:17, pp. 2887–2890, (1996).
W. A. Remers, J. Org. Chem., 36:9, pp. 1232–1239, (1971).
H. Ishibashi, Chem. Pharm. Bull., 42:2, pp. 271–276, (1994).
R. D. Dillard, et al., J. Med. Chem., 39:26, pp. 5119–5136, (1996).
R. D. Dillard, et al., J. Med. Chem., 39:26, pp. 5137–5158, (1996).
S. E. Draheim, J. Med. Chem., 1996, 39:26, pp. 5159–5175, (1996).

*Primary Examiner*—Laura L. Stockton
*Attorney, Agent, or Firm*—Arleen Palmberg

[57] ABSTRACT

A process for preparing 1H-indole-3-glyoxamides useful for inhibiting SPLA$_2$ and novel intermediates useful in the preparation of such compounds.

13 Claims, No Drawings

PROCESS FOR PREPARING 4-SUBSTITUTED-1H-INDOLE-3-GLYOXAMIDES

This application claims the benefit of U.S. Provisional Application No. 60/050,877, filed Jun. 26, 1997 and U.S. Provisional Application No. 60/050891, filed Jun. 26, 1997.

FIELD OF THE INVENTION

This invention relates to a process for preparing certain 1H-indole-3-glyoxamides useful for inhibiting sPLA$_2$ mediated release of fatty acids for conditions such as septic shock.

BACKGROUND OF THE INVENTION

Certain 1H-indole-3-glyoxamides are known to be potent and selective inhibitors of mammalian sPLA$_2$ useful for treating diseases, such as septic shock, adult respiratory distress syndrome, pancreatitis, trauma, bronchial asthma, allergic rhinitis, rheumatoid arthritis and related sPLA$_2$ induced diseases. EPO publication No. 0675110, for example, discloses such compounds.

Various patents and publications describe processes for making indole-3-glyoxamides.

The article, "Recherches en serie indolique. VI sur tryptamines substituees", by Marc Julia, Jean Igolen and Hanne Igolen, *Bull. Soc. Chim. France*, 1962, pp. 1060–1068, describes certain indole-3-glyoxylamides and their conversion to tryptamine derivatives.

The article, "2-Aryl-3-Indoleglyoxylamides (FGIN-1): A New Class of Potent and Specific Ligands for the Mitochondrial DBI Receptor (MDR)" by E. Romeo, et al., *The Journal of Pharmacology and Experimental Therapeutics*, Vol. 262, No. 3, (pp. 971–978) describes certain 2-aryl-3-indolglyoxylamides having research applications in mammalian central nervous systems.

The abstract, "Fragmentation of N-benzylindoles in Mass Spectrometry"; Chemical Abstracts, Vol. 67, 1967, 73028h, reports various benzyl substituted phenols including those having glyoxylamide groups at the 3 position of the indole nucleus.

U.S. Pat. No. 3,449,363 describes trifluoromethylindoles having glyoxylamide groups at the 3 position of the indole nucleus.

U.S. Pat. No. 3,351,630 describes alpha-substituted 3-indolyl acetic acid compounds and their preparation inclusive of glyoxylamide intermediates.

U.S. Pat. No. 2,825,734 describes the preparation of 3-(2-amino-1-hydroxyethyl)indoles using 3-indoleglyoxylamide intermediates such as 1-phenethyl-2-ethyl-6-carboxy-N-propyl-3-indoleglyoxylamide (see, Example 30).

U.S. Pat. No. 4,397,850 prepares isoxazolyl indolamines using glyoxylamide indoles as intermediates. U.S. Pat. No. 3,801,594 describes analgesics prepared using 3-indoleglyoxylamide intermediates.

The article, "No. 565.—Inhibiteurs d'enzymes. XII.—Preparation de (propargylamino-2 ethyl)-3 indoles" by A. Alemanhy, E. Fernandez Alvarez, O. Nieto Lopey and M. E. Rubio Herraez; *Bulletin De La Societe Chimique De France*, 1974, No. 12, pp. 2883–2888, describes various indolyl-3 glyoxamides which are hydrogen substituted on the 6-membered ring of the indole nucleus.

The article "Indol-Umlagerung von 1-Diphenylamino-2,3-dihydro-2,3-pyrrolidonen" by Gert Kollenz and Christa Labes; *Liebigs Ann. Chem.*, 1975, pp. 1979–1983, describes phenyl substituted 3-glyoxylamides.

Allowed U.S. application Ser. No. 08/469954, now U.S. Pat. No. 5,654,326, herein incorporated by reference in its entirety, discloses a process for preparing 4-substituted-1H-indole-3-glyoxamide derivatives comprising reacting an appropriately substituted 4-methoxyindole (prepared as described by Clark, R. D. et al., *Synthesis*, 1991, pp 871–878, the disclosures of which are herein incorporated by reference) with sodium hydride in dimethylformamide at room temperature (20–25° C.) then treating with arylmethyl halide at ambient temperatures to give the 1-arylmethylindole which is O-demethylated using boron tribromide in methylene chloride (Tsung-Ying Shem and Charles A. Winter, *Adv. Drug Res.*, 1977, 12, 176, the disclosure of which is incorporated by reference) to give the 4-hydroxyindole. Alkylation is achieved with an alpha bromoalkanoic acid ester in dimethylformamide using sodium hydride as a base. Conversion to the glyoxamide is achieved by reacting the -[(indol-4-yl)oxy]alkanoic acid ester first with oxalyl chloride, then with ammonia, followed by hydrolysis with sodium hydroxide in methanol.

The process for preparing 4-substituted-1H-indole-3-glyoxamide derivatives, as set forth above, has utility. However, this process uses expensive reagents and environmentally hazardous organic solvents, produces furan containing by-products and results in a relatively low yield of desired product.

The present invention provides an improved process for preparing 4-substituted-1H-indole-3-glyoxamide derivatives. The process of the present invention can be performed with inexpensive, readily available, reagents using aqueous solvent systems and resulting in better overall yield while avoiding the production of furan byproducts. Other objects, features and advantages of the present invention will become apparent from the subsequent description and the appended claims.

SUMMARY OF THE INVENTION

The present invention provides a process for preparing a compound of the formula I or a pharmaceutically acceptable salt or prodrug derivative thereof;

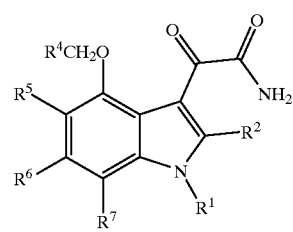

wherein:

R$^1$ is selected from the group consisting of C$_7$–C$_{20}$ alkyl;

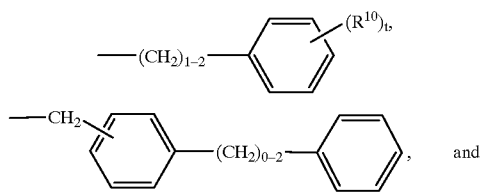

and

-continued

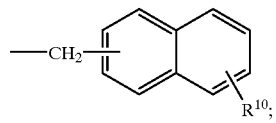

where

R$^{10}$ is selected from the group consisting of halo, $C_1$–$C_{10}$ alkyl, $C_1$–$C_{10}$ alkoxy, —S—($C_1$–$C_{10}$ alkyl) and halo($C_1$–$C_{10}$)alkyl, and t is an integer from 0 to 5 both inclusive;

R$^2$ is selected from the group consisting of hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), aryl, aryloxy, and HET;

R4 is selected from the group consisting of —CO$_2$H, —SO$_3$H, and —P(O)(OH)$_2$ or salt or prodrug derivatives thereof; and R$^5$, R$^6$ and R$^7$ are each independently selected from the group consisting of hydrogen, ($C_1$–$C_6$)alkyl, ($C_1$–$C_6$) alkoxy, halo($C_1$–$C_6$)alkoxy, halo($C_2$–$C_6$)alkyl, bromo, chloro, fluoro, iodo and aryl;

which process comprises the steps of:

a) halogenating a compound of formula X

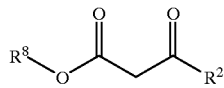

where R$^8$ is ($C_1$–$C_6$)alkyl, aryl or HET;
with SO$_2$Cl$_2$ to form a compound of formula IX

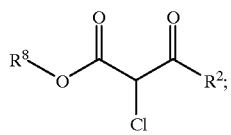

b) hydrolyzing and decarboxylating a compound of formula IX

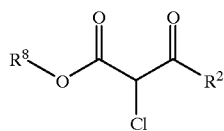

to form a compound of formula VIII

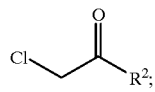

c) alkylating a compound of formula VII

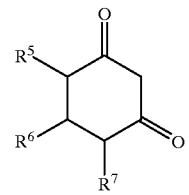

with a compound of formula VIII

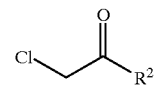

to form a compound of formula VI

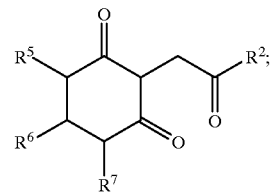

d) aminating and dehydrating a compound of formula VI

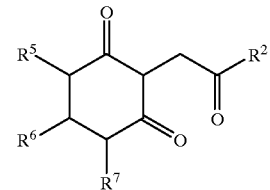

with an amine of the formula R$^1$NH$_2$ in the presence of a solvent that forms an azeotrope with water to form a compound of formula V;

e) oxidizing a compound of formula V

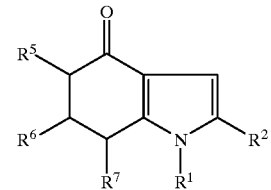

by refluxing in a polar hydrocarbon solvent having a boiling point of at least 150° C. and a dielectric constant of at least 10 in the presence of a catalyst to form a compound of formula IV

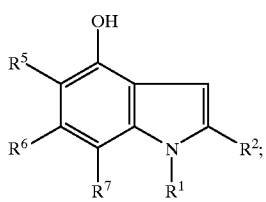

f) alkylating a compound of the formula IV

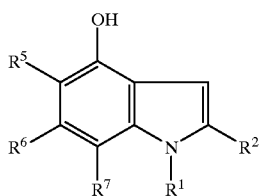

with an alkylating agent of the formula $XCH_2R^{4a}$ where X is a leaving group and $R^{4a}$ is $-CO_2R^{4b}$, $-SO_3R^{4b}$, $-P(O)(OR^{4b})_2$, or $-P(O)(OR^{4b})H$, where $R^{4b}$ is an acid protecting group, to form a compound of formula III

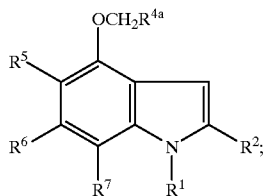

g) reacting a compound of formula III

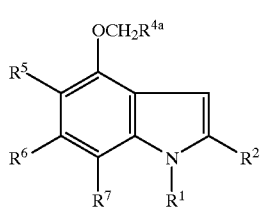

with oxalyl chloride and ammonia to form a compound of formula II

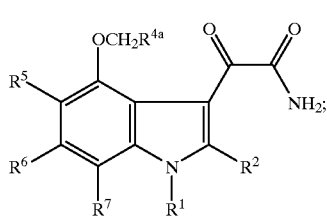

h) optionally hydrolyzing a compound of formula II

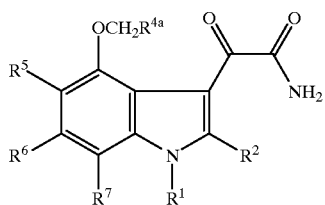

to form a compound of formula I; and i) optionally salifying a compound of formula I.

In another embodiment of the invention is provided a process for preparing a compound of formula I comprising the steps of:

a) oxidizing a compound of the formula V

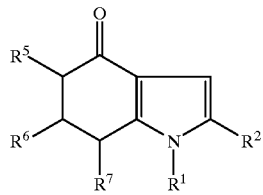

by refluxing in a polar hydrocarbon solvent having a boiling point of at least 150° C. and a dielectric constant of at least 10 in the presence of a catalyst to form a compound of formula IV

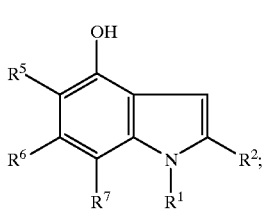

b) alkylating a compound of the formula IV

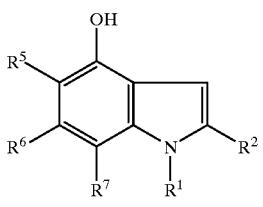

with an alkylating agent of the formula $XCH_2R^{4a}$ where X is a leaving group and $R^{4a}$ is $-CO_2R^{4b}$, $-SO_3R^{4b}$, $-P(O)(OR^{4b})_2$ or $-P(O)(OR^{4b})H$, where $R^{4b}$ is an acid protecting group, to form a compound of formula III c) reacting a compound of formula III

[Structure III: indole with OCH$_2$R$^{4a}$ at 4-position, R$^5$, R$^6$, R$^7$ on benzene ring, R$^2$ at 2-position, R$^1$ on N]

with oxalyl chloride and ammonia to form a compound of formula II

[Structure II: same indole with C(O)C(O)NH$_2$ at 3-position]

d) optionally hydrolyzing a compound of formula II

[Structure II repeated]

to form a compound of formula I; and
e) optionally salifying a compound of formula I.

The present invention, further, provides new intermediate compounds of the formula IV

[Structure IV: indole with OH at 4-position, R$^5$, R$^6$, R$^7$ on benzene ring, R$^2$ at 2-position, R$^1$ on N]

wherein:
R$^1$ is selected from the group consisting of —C$_7$–C$_{20}$ alkyl,

[Structures: —(CH$_2$)$_{1-2}$-phenyl-(R$^{10}$)$_t$; —CH$_2$-phenyl-(CH$_2$)$_{0-2}$-phenyl, and —CH$_2$-naphthyl-R$^{10}$;]

where
R$^{10}$ is selected from the group consisting of halo, C$_1$–C$_{10}$ alkyl, C$_1$–C$_{10}$ alkoxy, —S—(C$_1$–C$_{10}$ alkyl) and halo(C$_1$–C$_{10}$)alkyl, and t is an integer from 0 to 5 both inclusive;

R$^2$ is selected from the group consisting of hydrogen, halo, C$_1$–C$_3$ alkyl, C$_3$–C$_4$ cycloalkyl, C$_3$–C$_4$ cycloalkenyl, —O—(C$_1$–C$_2$ alkyl), —S—(C$_1$–C$_2$ alkyl), aryl, aryloxy and HET; and R$^5$, R$^6$ and R$^7$ are each independently selected from the group consisting of hydrogen, (C$_1$–C$_6$)alkyl, (C$_1$–C$_6$)alkoxy, halo(C$_1$–C$_6$)alkoxy, halo(C$_2$–C$_6$)alkyl, bromo, chloro, fluoro, iodo and aryl.

The compounds of formula IV are useful as intermediates in preparing the compounds of formula I.

The present invention provides, in addition, a process for preparing a compound of formula IV

[Structure IV]

comprising the steps of:
a) halogenating a compound of formula X

[Structure X: R$^8$-O-C(O)-CH$_2$-C(O)-R$^2$]

where R$^8$ is (C$_1$–C$_6$)alkyl, aryl or HET;
with SO$_2$Cl$_2$ to form a compound of formula IX

[Structure IX: R$^8$-O-C(O)-CHCl-C(O)-R$^2$]

b) hydrolyzing and decarboxylating a compound of formula IX

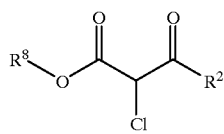

to form a compound of formula VIII

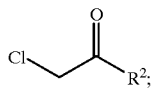

c) alkylating a compound of formula VII

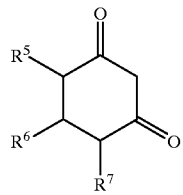

with a compound of formula VIII

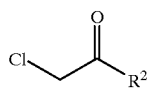

to form a compound of formula VI

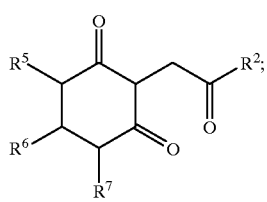

d) aminating and dehydrating a compound of formula VI

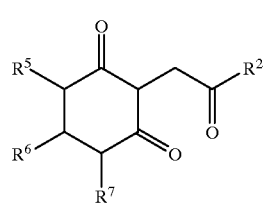

with an amine of the formula $R^1NH_2$ in the presence of a solvent that forms an azeotrope with water to form a compound of formula V

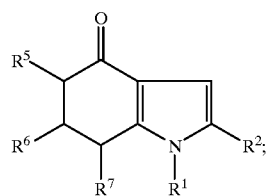

e) oxidizing a compound of formula V

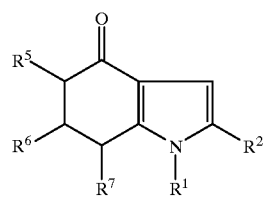

by refluxing in a polar hydrocarbon solvent having a boiling point of at least 150° C. and a dielectric constant of at least 10 in the presence of a catalyst.

In another embodiment, the present invention provides a process for preparing a compound of formula IV comprising:

oxidizing a compound of formula V

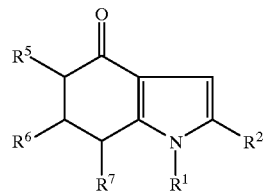

by refluxing in a polar hydrocarbon solvent having a boiling point of at least 150° C. and a dielectric constant of at least 10 in the presence of a catalyst.

DETAILED DESCRIPTION OF THE INVENTION

The 1H-indole-3-glyoxylamides of the invention employ certain defining terms as follows:

As used herein, the term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, tert-butyl, n-pentyl, isopentyl, neopentyl, heptyl, hexyl, octyl, nonyl, decyl, and the like.

The term "$(C_1-C_{10})$alkoxy", as used herein, denotes a group such as methoxy, ethoxy, n-propoxy, isopropoxy, n-butoxy, t-butoxy, n-pentoxy, isopentoxy, neopentoxyl, heptoxy, hexoxy, octoxy, nonoxy, decoxy and like groups, attached to the remainder of the molecule by the oxygen atom.

The term "$(C_3-C_4)$cycloalkyl" includes cyclopropyl, and cyclobutyl groups

The term "$C_3-C_4$ cycloalkenyl" includes a cyclopropenyl or cyclobutenyl ring having a double bond at the 1- or 2-position.

The term "halo" means fluoro, chloro, bromo or iodo.

The term "halo($C_1$–$C_{10}$)alkyl" means a ($C_1$–$C_{10}$)alkyl group, substituted with from 1 to 3 halo atoms, attached to the remainder of the molecule by the alkyl group. The term halo($C_1$–$C_{10}$)alkyl includes the term halo($C_2$–$C_6$)alkyl.

The term "halo($C_1$–$C_6$)alkoxy" means a halo-substituted alkoxy group which group is attached to the remainder of the molecule at the oxygen of the alkoxy.

The term "aryl" means a group having the ring structure characteristic of benzene, pentalene, indene, naphthalene, azulene, heptalene, phenanthrene, anthracene, etc. The aryl group may be optionally substituted with 1 to 3 substituents selected from the group consisting of ($C_1$–$C_6$)alkyl (preferably methyl), ($C_1$–$C_6$)alkoxy or halo (preferable fluorine or chlorine).

The term "aryloxy" means an aryl group attached to the remainder of the molecule by an oxygen linker.

The term "leaving group" means a substituent with an unshared electron pair that departs from the substrate in a nucleophilic substitution reaction. The term "leaving group" includes halo, sulfonate, acetate and the like.

The term HET includes pyridine, pyrazine, pyrimidine, pyridazine, pyrrole, pyrazole, furan, thiophene, thiazole, isothiazole, oxadiazole, thiadiazole, imidazole, triazole and tetrazole. The heterocyclic ring can be attached to the remainder of the molecule by any carbon in the heterocyclic ring.

The salts of the compounds of formula I are an additional aspect of the invention. In those instances where the compounds of the invention possess acidic functional groups various salts may be formed which are more water soluble and physiologically suitable than the parent compound. Representative pharmaceutically acceptable salts include but are not limited to the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)).

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters.

The term "acid protecting group" is used herein as it is frequently used in synthetic organic chemistry, to refer to a group which will prevent an acid group from participating in a reaction carried out on some other functional group of the molecule, but which can be removed when it is desired to do so. Such groups are discussed by T. W. Greene in chapter 5 of *Protective Groups in Organic Synthesis*, John Wiley and Sons, New York, 1981, incorporated herein by reference in its entirety.

Examples of acid protecting groups includes ester or amide derivatives of the acid group, such as methyl, methoxymethyl, methyl-thiomethyl, tetrahydropyranyl, methoxyethoxymethyl, benzyloxymethyl, phenylaryl, ethyl, 2,2,2-trichloroethyl, 2-methylthioethyl, t-butyl, cyclopentyl, triphenylmethyl, p-bromobenzyl, trimethylsilyl, N,N-dimethyl, pyrrolidinyl, piperidinyl or o-nitroanilide. A preferred acid-protecting group is methyl.

Preferred Compounds Made By the Process of the Invention

A preferred group of compounds of formula I prepared by the process of the instant invention are those wherein:

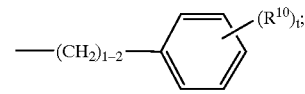

$R^1$ is $R^2$ is halo, cyclopropyl, methyl, ethyl, propyl, O-methyl or S-methyl;

$R^4$ is —$CO_2H$; and $R^5$, $R^6$ and $R^7$ are H.

Compounds which can be made by the process of the instant invention include:

((3-(2-amino-1,2-dioxyethyl)-2-methyl-1-(phenylmethyl)-1H-indol-4-yl)oxy)acetic acid;

dl-2-((3-(2-amino-1,2-dioxyethyl)-2-methyl-1-(phenylmethyl)-1H-indol-4-yl)oxy)propanoic acid;

((3-(2-amino-1,2-dioxyethyl)-1-(((1,1'-biphenyl)-2-ylmethyl)-2-methyl-1H-indol-4-yl)oxy)acetic acid;

((3-(2-amino-1,2-dioxyethyl)-1-((1,1'-biphenyl)-3-ylmethyl)-2-methyl-1H-indol-4-yl)oxy)acetic acid;

((3-(2-amino-1,2-dioxyethyl)-1-((1,1'-biphenyl)-4-ylmethyl)-2-methyl-1H-indol-4-yl)oxy)acetic acid;

((3-(2-amino-1,2-dioxyethyl)-1-((2,6-dichlorophenyl)methyl)-2-methyl-1H-indol-4-yl)oxy)acetic acid;

((3-(2-amino-1,2-dioxyethyl)-1-(4-fluorophenyl)methyl)-2-methyl-1H-indol-4-yl)oxy)acetic acid;

((3-(2-amino-1,2-dioxyethyl)-2-methyl-1-((naphthalenyl)methyl)-1H-indol-4-yl)oxy)acetic acid;

((3-(2-amino-1,2-dioxyethyl)-2-ethyl-1-(phenylmethyl)-1H-indol-4-yl)oxy)acetic acid;

((3-(2-amino-1,2-dioxyethyl)-1-((3-chlorophenylmethyl)-2-ethyl-1H-indol-4-yl)oxy)acetic acid;

((3-(2-amino-1,2-dioxyethyl)-1-((1,1'biphenyl)-2-ylmethyl)-2-ethyl-1H-indol-4-yl)oxy)acetic acid;

((3-(2-amino-1,2-dioxyethyl)-1-((1,1'-biphenyl)-2-ylmethyl)-2-propyl-1H-indol-4-yl)oxy)acetic acid;

((3-(2-amino-1,2-dioxyethyl)-2-cyclopropyl-1-(phenylmethyl)-1H-indol-4-yl)oxy)acetic acid;

((3-(2-amino-1,2-dioxyethyl)-1-((1,1'biphenyl)-2-ylmethyl)-2-cyclopropyl-1H-indol-4-yl)oxy)acetic acid;

4-((3-(2-amino-1,2-dioxyethyl)-2-ethyl-1-(phenylmethyl)-1H-indol-4-yl)oxy)butanoic acid;

((3-(2-amino-1,2-dioxyethyl)-2-ethyl-1-(phenylmethyl)-1H-indol-4-yl)oxyacetic acid;

((-3-(2-amino-1,2-dioxyethyl)-2-ethyl-6-methyl-1-(phenylmethyl)-1H-indol-4-yl)oxy)acetic acid;
((-3-(2-amino-1,2-dioxyethyl)-2,6-dimethyl-1-(phenylmethyl)-1H-indol-4-yl)oxy)acetic acid;
((3-(2-amino-1,2-dioxyethyl)-2-methyl-1-(phenylmethyl)-1H-indol-4-yl)oxy)acetic acid;
((3-(2-amino-1,2-dioxyethyl)-6-ethyl-2-methyl-1-(phenylmethyl)-1H-indol-4-yl)oxy)acetic acid;
((3-(2-amino-1,2-dioxyethyl)-2,6-diethyl-1-(phenylmethyl)-1H-indol-4-yl)oxy)acetic acid;
((3-(2-amino-1,2-dioxyethyl)-2-methyl-6-phenoxy-1-(phenylmethyl)-1H-indol-4-yl)oxy)acetic acid;
((3-(aminooxoacetyl)-2-ethyl-6-methyl-1-(phenylmethyl)-1H-indol-4-yl)oxy)acetic acid; and
((3-(2-amino-1,2-dioxyethyl)-2-ethyl-6-phenoxy-1-(phenylmethyl)-1H-indol-4-yl)oxy)acetic acid or a pharmaceutically acceptable salt thereof.

Of these compounds, preferred compounds include:
((3-(2-amino-1,2-dioxyethyl)-2-ethyl-1-(phenylmethyl)-1H-indol-4-yl)oxyacetic acid;
((-3-(2-amino-1,2-dioxyethyl)-2-ethyl-6-methyl-1-(phenylmethyl)-1H-indol-4-yl)oxy)acetic acid;
((-3-(2-amino-1,2-dioxyethyl)-2,6-dimethyl-1-(phenylmethyl)-1H-indol-4-yl)oxy)acetic acid;
((3-(2-amino-1,2-dioxyethyl)-2-methyl-1-(phenylmethyl)-1H-indol-4-yl)oxy)acetic acid;
((3-(2-amino-1,2-dioxyethyl)-6-ethyl-2-methyl-1-(phenylmethyl)-1H-indol-4-yl)oxy)acetic acid;
((3-(2-amino-1,2-dioxyethyl)-2,6-diethyl-1-(phenylmethyl)-1H-indol-4-yl)oxy)acetic acid;
((3-(2-amino-1,2-dioxyethyl)-2-methyl-6-phenoxy-1-(phenylmethyl)-1H-indol-4-yl)oxy)acetic acid;
((3-(aminooxoacetyl)-2-ethyl-6-methyl-1-(phenylmethyl)-1H-indol-4-yl)oxy)acetic acid; and
((3-(2-amino-1,2-dioxyethyl)-2-ethyl-6-phenoxy-1-(phenylmethyl)-1H-indol-4-yl)oxy)acetic acid or a pharmaceutically acceptable salt thereof Of these compounds even more preferred are ((3-(2-amino-1,2-dioxyethyl)-2-methyl-1-(phenylmethyl)-1H-indol-4-yl)oxy)acetic acid and ((3-(2-amino-1,2-dioxyethyl)-2-ethyl-1-(phenylmethyl)-1H-indol-4-yl) oxyacetic acid.

The most preferred compound which can be prepared by the instant process is ((3-(2-amino-1,2-dioxyethyl)-2-ethyl-1-(phenylmethyl)-1H-indol-4-yl)oxyacetic acid or a pharmaceutically acceptable salt thereof.

Compounds of formula IV wherein $R^1$ is

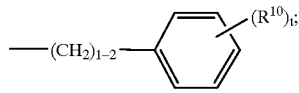

$R^2$ is halo, cyclopropyl, methyl, ethyl, propyl, O-methyl or S-methyl and $R^5$, $R^6$ and $R^7$ are H are preferred intermediates in the process for making the compounds of formula I.

The most preferred compound of formula IV is 2-ethyl-1-(phenylmethyl)-4-hydroxy-1H-indole.

Further typical examples of compounds of formula IV which are useful in the present invention include:
2-chloro-1-(3-methylphenylethyl)-4-hydroxy-6-methoxy-1H-indole;
2-cyclopropyl-1-(4-ethylthiophenylmethyl)-4-hydroxy-5-(2-fluorobutoxy)-1H-indole;
2-(cycloprop-1-enyl)-1-(5-chloroheptylphenylethyl)-4-hydroxy-5,7-difluoro-1H-indole;
2-methoxy 1-(3-t-butylphenylmethyl)-4-hydroxy-7-phenyl1H-indole;
2-methylthio-1-(4-phenylethylphenylmethyl)-4-hydroxy-6-iodo-1H-indole;
2-phenyl-1-heptyl-4-hydroxy-1H-indole;
2-naphthyl-1-octyl-4-hydroxy-6-hexyl-1H-indole;
2-cyclobutyl-1-dodecyl-4-hydroxy-1H-indole;
2-(cyclobut-1-enyl)-1-(2-chlorophenylmethyl)-4-hydroxy-7-butoxy-1H-indole;
2-cyclopropyl-1-octadecyl-4-hydroxy-5-(3-fluorohexoxy)-1H-indole;
2-(cycloprop-1-enyl)-1-(3-pentoxyphenylethyl)-4-hydroxy-6-methyl-1H-indole;
2-methoxy-1-(2-phenylmethylphenylmethyl)-4-hydroxy-7-(2-chloroethyl)-1H-indole;
2-ethylthio-1-tetradecyl-4-hydroxy-5,7-dibromo-1H-indole.

Process of the Invention

The process of the present invention provides an improved method for synthesizing the compounds of formula I using inexpensive, readily available reagents as shown in Scheme I as follows.

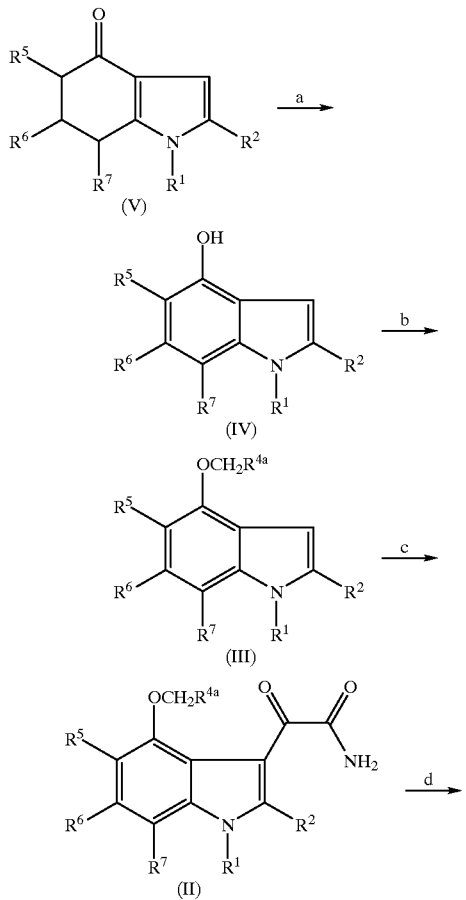

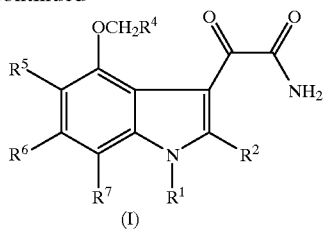

A compound of formula V is dissolved in a polar hydrocarbon solvent, having a boiling point of at least 150° C. and a dielectric constant of at least 10° C., such as diethylene glycol, CELLOSOLVE®, CARBITOL®, glyme, diglyme or triglyme. CARBITOL is preferred in the instant process. The amount of solvent used should be sufficient to ensure that all compounds stay in solution until the desired reaction is complete.

Solvents having a boiling point of from 150° C. to 250° C. and a dielectric constant of 10 to 20 are preferred. Solvents with a boiling point in the range of from 150° C. to 220° C. and a dielectric constant of from 12 to 18 are most preferred.

Examples of other suitable solvents include m-dichlorobenzene, bromobenzene, m-toluidine, o-toluidine, trans-3-methylcyclohexanol, 1,1,2,2-tetrachloroethane, 2-heptanol, 2-butoxyethanol, o-dichlorobenzene, cresol, 1-octanol, 3-methylcyclohexanol, benzyl alcohol, 2-methylcyclohexanol, 4-methylcyclohexanol, octanenitrile, hexanenitrile, alpha-tolunitrile, 1,1,2,2-tetramethylurea and triethyleneglycol.

The solution is heated, preferably to the reflux temperature of the solvent selected. It is desirable to conduct the reaction in the presence of a catalyst, such as Pd/C, Pt/C, PdO, $PtO_2$, $V_2O_5$, CuO, NiO, DDQ or $MnO_2$. Palladium on carbon and palladium oxide are preferred. The reaction is substantially complete in about 30 minutes to 24 hours.

Indole (IV) may then be readily alkylated with an alkylating agent of the formula $XCH_2R^{4a}$ where X is a suitable leaving group and $R^{4a}$ is a protected carboxy, sulfonyl or phosphonyl acid group, preferably protected with an ester group, in the presence of a base. Methyl bromoacetate is a preferred alkylating agent. Suitable bases include potassium carbonate, sodium carbonate, lithium carbonate, cesium carbonate, sodium bicarbonate, potassium bicarbonate or potassium hydroxide. Potassium carbonate is preferred. The amount of alkylating agent is not critical, however, the reaction is best accomplished using a molar excess of alkylating agent relative to the starting material. The reaction is preferably carried out in an organic solvent such as acetone, acetonitrile or dimethylformanide. Other suitable solvents include tetrahydrofuran, methyl ethyl ketone, acetonitrile, or t-butyl methylether. The reaction is conducted at temperatures of from about 0° to 100° C., preferably at ambient temperature, and is substantially complete in about 1 to 24 hours depending on the reactants employed and such conditions as reaction temperature.

Optionally, a phase transfer reagent such as tetrabutylammoniumbromide may be employed.

Preparation of glyoxamide II is readily achieved in a two step process by first treating intermediate III with oxalyl chloride at concentrations from about 0.2 to 1.5 mmol, preferably at equimolar concentrations relative to the starting material. Solvents such as methylene chloride, chloroform, trichloroethylene, carbon tetrachloride, ether or toluene are preferred. Temperatures from about -20° C. to ambient temperature are suitable, preferably about -5° C.

In the second step, the solution is treated with ammonia; either bubbled in as a gas or, preferably, using a molar excess of 30% aqueous ammonia. The reaction is typically conducted at temperatures from about -25° C. to 25° C., preferably at about -2° C. to 0° C., and is substantially complete in 10 minutes to an hour.

Hydrolysis of II is achieved using a base such as potassium hydroxide, lithium hydroxide or sodium hydroxide, preferably sodium hydroxide, in a lower alcohol solvent, such as methanol, ethanol, isopropanol, etc., or solvents such as tetrahydrofuran, dioxane and acetone.

Using standard analytical techniques, such as HPLC, the reactions of Scheme I can be monitored to determine when starting materials and intermediates are converted to product.

Starting material V is prepared according to the following procedure.

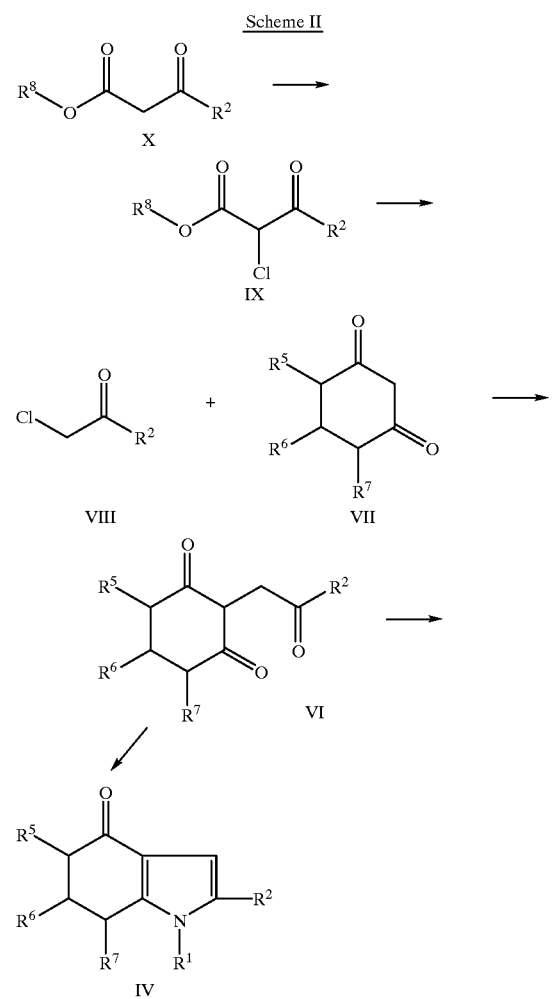

$R^8$ is $(C_1-C_6)$ alkyl or aryl

An appropriately substituted propionylacetate X is first halogenated by treatment with sulfuryl chloride, preferably at equimolar concentrations relative to the starting material, at temperatures of from about 0° C. to 25° C., preferably less than 15° C., to prepare IX.

Hydrolysis and decarboxylation of IX is achieved by refluxing with an aqueous acid, such as hydrochloric acid, for from about 1 to 24 hours. The solution containing the decarboxylated product VIII is neutralized to adjust the pH to about 7.0–7.5, then reacted with cyclohexanedione VII (preferably at equimolar concentrations) and a base, preferably sodium hydroxide, to yield the triketone monohydrate VI as a precipitate which may be purified and isolated, if desired. The reaction is preferably conducted at temperatures of from −20° C. to ambient temperatures and is substantially complete in about 1 to 24 hours.

The above reactions are preferably run as a "one pot" process with the reactants added to the reaction vessel in the order given above. Preferably, the reaction is allowed to proceed without isolating compounds of formula IX or VIII, thus avoiding exposure to these volatile lachrymators.

Preparation of V is achieved by refluxing VI in a high boiling non-polar solvent which forms an azeotrope with water, preferably toluene, with an equimolar quantity of an amine of the formula $R^1NH_2$, where $R^1$ is as defined above. Solvents with a boiling point of at least 100° C. are preferred, such as toluene, xylene, cymene, benzene, 1,2-dichloroethane or mesitylene, thus eliminating the need for a pressure reactor. Sufficient solvent should be employed to ensure that all compounds stay in solution until the reaction is substantially complete in about 1 to 24 hours.

Alternately, intermediate IV can be prepared from VI in a one pot process without isolating intermediate V by heating VI with palladium on carbon and an appropriately substituted amine of the formula $R^1NH_2$ in a polar hydrocarbon solvent such as CARBITOL® as described in Scheme I above. The reaction is preferably run at reflux and is substantially complete in one to 24 hours.

Method of Making Intermediate Compound of Formula IV

Intermediate IV can be prepared as described in Schemes I, step a, and II above.

The intermediate hydroxyindole IV can be purified using standard crystallization procedures. For example, filtration of the reaction product over diatomaceous earth followed by t-butylmethylether rinses effectively removes the catalyst. The filtrate can then be diluted with additional t-butylmethylether and rinsed, preferably with water. The organic phase is collected, dried and concentrated by conventional means. The concentrate is preferably dissolved in methylene chloride/hexanes, filtered over silicon dioxide and reconcentrated.

Standard analytical techniques, such as HPLC, can be used to monitor the reactions in order to determine when the starting material and intermediates are converted to product.

It will be readily appreciated by the skilled artisan that the starting materials for all the above procedures are either commercially available or can be readily prepared by known techniques from commercially starting materials. For example, starting material X can be readily prepared as described by D. W. Brooks et al., *Angew. Chem., Int. Ed. Eng* 1979, 18, 72. Other preparations are described by R. J. Cregge, et. al., *Tetrahedron Lett.* 1973, 26, 2425; M. W. Rathke, et al., *J. Am. Chem. Soc.* 1971. 93, 2318; M. Hirama, et al., *Tetrahedron Lett.*, 1986, 27, 5281; D. F. Taber, et al., *J. Am. Chem. Soc.* 1987, 109, 7488; and T. Hanken, *Chem Ind.* 1973, 325.

Preparation of starting material VII can be accomplished, for example, in a Dieckman cyclization as described by Gramatiga P, et al., *Heterocycles* 24(3), 743–750(1986) or Frank R. L. et al., *J. Am. Chem Soc*, 72, p. 1645, 1950 Additional preparations can be found, among others, in Venkar Y. D. et al., *Tetrahedron Lett*, 28, p. 551, 1987; H. E. Zimmerman et al., *J. Am. Chem. Soc.*, 107 (25), p. 7732, 1985; Hosangadi B. D., et al, *Indian J. Chem.*, 20, mp. 63, 1981; Zenyuk A.A. et al., *Zh Org Khim* 26(10), 2232–2233 (1990); or Berry N. M. et al., *Synthesis-Stuttgart* (6), 476–480 (1986).

The following examples further illustrate the process of the present invention. The examples also illustrate the preparation of the intermediate compounds of this invention. The examples are illustrative only and not intended to limit the scope of the invention in any way.

The following abbreviations are used in the Examples below:

HCl is hydrochloric acid
NaOH is sodium hydroxide
Pd/C is palladium on carbon
t-BuOMe is t-butylmethylether
$MgSO_4$ is magnesium sulfate
$CH_2Cl_2$ is dichloromethane
$SiO_2$ is silicon dioxide
$K_2CO_3$ is potassium carbonate
i-PrOH is isopropyl alcohol
$NH_3(g)$ is ammonia gas
MeOH is methanol
EtOH is ethanol
MTBE is tert-butyl methyl ether Preparation 2-ethyl-(phenylmethyl)-1)H-indole-4-Ol

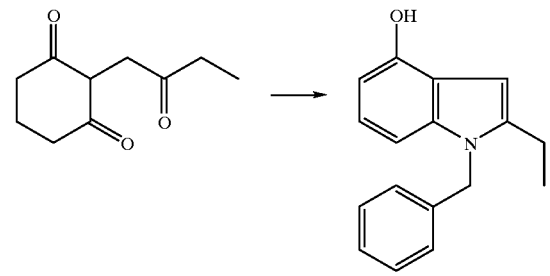

750 g (4.12 mol) of 2-(2-oxobutyl)-1,3-cyclohexanedione was added to a 22 L flask, followed by 75 g of 10% Pd/C and then 7.5 L of carbitol (lot 119WC7) with stirring. To the flask, 462 g (4.32 mol) of benzylamine was added and heated to 200° C. for approximately 1 hour. The reaction was allowed to reflux (at 197° C.) for 1 hour. TLC showed no starting material. The reaction was cooled to room temperature, filtered through celite to remove the catalyst, the solids were washed with 6.0 L of toluene, then 2 L of water. To the filtrate was added 12 L toluene and 6 L water. The mixture was stirred and the layers were separated. The aqueous layer was back extracted with 2×4 L of methylene chloride. All organic layers were combined and concentrated to an oil weighing 1008 g. This oil was filtered through a silica gel plug using methylene chloride to elute product from silica. All fractions containing product were combined and concentrated to a solid (775 g). The solid was dissolved in 2 L of toluene at 65° C., stirred for 15 minutes then diluted with 15 L of cyclohexane, and stirred 10 minutes at 65–70°

C. After cooling to room temperature, the product crystallized and was placed in a chiller (0° C.) overnight, then stirred cold for 15–30 minutes, filtered and washed with 2.0 L of cyclohexane. The product was vacuum dried to a constant weight. 547.4g. Yield=52.9

EXAMPLE 1

((3-(aminooxoacetyl)-2-ethyl-1-(phenylmethyl)-1H-indol-4-yl)oxy)acetic acid

A. Preparation of 2-(2-oxobutyl)-1,3-cyclohexanedione

Methyl propionylacetate (130.15 g, 1.0 mol) was placed into a 2 L Morton flask equipped with a mechanical stirrer, nitrogen inlet and thermocouple. External cooling was applied until the internal temperature was 10° C. Sulfuryl chloride (135 g, 1.0 mol) was added dropwise at a rate to maintain the temperature <15° C. Upon complete addition, chromatographic analysis indicated the total conversion to the desired chloro-compound. 1M HCl (205 mL) was then added, and the reaction mixture was stirred at reflux for 18 hours. After cooling to room temperature, 4N NaOH was added to adjust the pH to 7.0 to 7.5. Cyclohexanedione (112.13 g, 1.0 mol) was added and the mixture was cooled in an ice bath. Then, 5N NaOH (200 mL, 1.0 mol) was added dropwise and the reaction was stirred for 18 hours at room temperature. The resulting thick precipitate was filtered, rinsed with water, and dried in vacuo to yield the subtitled triketone monohydrate, 101 g, 56%.

m.p 96–98° C.; $R_f$=0.63($SiO_2$/9:1 $CH_2Cl_2$:i-PrOH). $^1$H NMR ($CDCl_3$)δ 1.04(t, 3H, J=7.2Hz), 1.93(m, 2H),2.35(m, 2H), 2.50 (m, 2H), 2.63 (q, 2H, J=7.2 Hz), 3.51 (s, 2H), 9.97 (s, 1H). IR($CHCl_3$)3018, 1707, 1613, 1380, 1189, 1127 cm$^{-1}$. UV(EtOH) $\lambda_{max}$ (ε)=262 (14500). EA Theory: C, 59.98 H, 8.05; Found: C, 59.71 H, 7.82. MS for $C_{10}H_{14}O_3$: m/z=183 (m+1).

B. Preparation of 2-ethyl-1,5,6,7-tetrahydro-1-(phenylmethyl)-4H-indol-4-one

The triketone thus obtained above, 101.14 g (0.51 mol) was placed into a 2000 mL flask equipped with a Dean-Stark water separator, mechanical stirrer and dropping funnel. Toluene (600 mL) was added and the mixture was heated to reflux until the distillate became clear and all water was removed. The reaction mixture was cooled slightly, while benzylamine (55 g, 0.51 mol) was added dropwise causing an exothermic reaction with the generation of water. Upon complete addition, the reaction was brought to reflux with continued azeotropic water removal (3 hours). Chromatographic analysis indicated that the triketone was completly consumed. The light yellow solution was then cooled to room temperature, whereupon the color changed to brown. The toluene solution was concentrated to dryness and the resulting brown oil (133.8 g) was used directly in the subsequent oxidation.

m.p. 59–61° C.; $R_f$=0.37($SiO_2$/2:1:1 hexane:$CH_2Cl_2$:EtOAc). $^1$H NMR ($CDCl_3$)δ 1.91(t, 2H, J=7.4 Hz), 2.80–2.12 (m, 2H), 2.42–2.48 (m, 4H), 2.60–2.64 (m,2H), 5.03 (s, 2H), 6.38(s, 1H), 6.89–6.91 (m, 2H), 7.28–7.32 (m, 3H). $^{13}$C NMR (DMSO-$d_6$) δ 12.9, 19.2, 21.9, 23.9, 38.0, 46.9, 101.7, 119.7, 126.4, 127.7, 129.3, 137.0, 138.0, 144.4, 192.8. IR (KBr) 1640, 1453, 1175, 1137 cm$^{-1}$. UV (EtOH) $\lambda_{max}$ (ε)=284 (7500), 252 (11000), 208 (199000). EA Theory: C,80.60 H,7.56 N,5.53; Found: C,80.80 H,7.67 N,5.56. MS for $C_{17}H_{19}NO$: m/z=253.

C. Preparation of 2-ethyl-(phenylmethyl)-1H-indol-4-ol

A 2000 mL 3 neck Morton flask was equipped with a mechanical stirrer, reflux condenser and stopper. The flask was charged with 10% Pd/C (26.8 g), followed by a solution of the compound of step B above, (133.8 g) in Carbitol® (800 mL, 2-ethoxy(ethoxy)ethanol). The resulting mixture was then brought to reflux for 18 hours. After cooling, filtration over diatomaceous earth followed by t-BuOMe rinses effectively removed the catalyst. The filtrate was diluted with a total of 1 L t-BuOMe, and rinsed with water (3×2 L). The organic phase was dried over $MgSO_4$ and concentrated to yield 166 g of dark brown oil. The oil was dissolved in $CH_2Cl_2$:hexanes (3:1) and filtered over $SiO_2$ (325 g), eluting with additional solvent until colorless. Concentration afforded 132.7 g of subtitled indole.

m.p. 98.5–100° C.; $R_f$=0.74($SiO_2$/2:1:1 Hexanes: $CH_2Cl_2$:EtOAc). $^1$H NMR ($CDCl_3$)δ 1.32 (t, 3H, J=7.4 Hz), 2.67 (q, 2H, J=7.4 Hz), 4.96 (s, 1H), 5.29 (s, 2H), 6.39 (s, 1H), 6.51 (d, 1H, J=7.9 Hz), 6.82 (d, 1H, J=8.2 Hz), 6.94–6.99 (m, 3H), 7.23–7.26 (m, 3H). $^{13}$C NMR (DMSO-$d_6$) δ 13.1, 19.9, 46.4, 96.2, 101.8, 104.3, 118.0, 122.1, 126.6, 127.5, 129.1, 139.2, 139.5, 141.0, 150.6. IR (KBr) 1586, 1467, 1351, 1250 cm$^{-1}$. UV (EtOH) $\lambda_{max}$ (ε)=296 (6700), 287 (6500), 269 (8200) 223 (35000). EA Theory: C, 81.24 H, 6.82 N, 5.57; Found: C, 80.98 H, 6.90 N, 5.59. MS for $C_{17}H_{17}NO$: m/z=251.

D. Preparation of ((2-ethyl-1-(phenylmethyl)-1H-indol-4-yl)oxy)acetic acid methyl ester Compound of part C, above, (3.0 g, 12.0 mmol), $K_2CO_3$ (3.31 g, 24.0 mmol) and acetone (24 mL) were charged to a 100 mL round bottom flask equipped with a magnetic stirrer. The heterogenous reaction mixture was stirred at room temperature for 20 minutes. Methyl bromoacetate (1.7 mL, 18.0 mmol) was added dropwise via syringe, and the reaction mixture was stirred for an additional 15 hours. The reaction mixture was filtered on a Buchner funnel, the solid washed with acetone and the filtrate was passed over fluted filter paper. The acetone was concentrated in vacuo to yield 4.1 g as a white solid. Crystallization from i-PrOH (30 mL) provided 3.28 g (84.5%) of the desired substituted intermediate as a colorless crystalline solid.

m.p. 95.5–97° C.; $R_f$=0.74($SiO_2$/$CH_2Cl_2$). $^1$H NMR ($CDCl_3$)δ 1.32 (t, 3H, J=7.4 Hz), 2.67 (q, 2H, J=7.4 Hz), 4.96 (s, 1H), 5.29 (s, 2H), 6.39 (s, 1H), 6.51 (d, 1H, J=7.9 Hz), 6.82 (d, 1H, J=8.2 Hz), 6.94–6.99 (m, 3H), 7.23–7.26 (m, 3H). $^{13}$C NMR ($CDCl_3$) δ 12.6, 20.0, 46.7, 52.2, 65.9, 96.0, 101.1, 104.0, 118.8, 121.4, 125.9, 126.0, 127.3, 128.8, 137.9, 139.1, 141.9, 151.1, 169.9. IR ($CHCl_3$) 3009, 1761, 1739, 1498, 1453, 1184, 1112 cm$^{-1}$ UV (EtOH) $\lambda_{max}$ (ε)= 221 (36500), 271 (9600), 283 (7800), 293 (7700). EA Theory: C, 74.28 H, 6.55 N, 4.33; Found: C, 73.32 H, 6.64 N,4.19. MS for $C_{20}H_{21}NO_3$: m/z=324 (m+1).

E. Preparation of ((3-(2-amino-1,2-dioxyethyl)-2-ethyl-1-(phenylmethyl)-1H-indol-4-yl)oxy)acetic acid methyl ester Compound of part D, above, (4.0 g, 0.0124 mole) was charged to a 100 ml 3 neck round bottom flask equipped with a $N_2$ inlet, magnetic stirrer, and gas dispersion tube connected to an $NH_3$ tank. Dichloromethane (28 mL) was added, resulting in a yellow solution, which was cooled via an ice bath. To the chilled solution, neat oxalyl chloride (1.1 mL, 0.012 mol) was added slowly by syringe forming a dark green solution. After stirring the reaction solution for 20 minutes at ice bath temperature, chromatographic analysis (TLC $SiO_2$, $CH_2Cl_2$) indicated the absence of starting material. $NH_3$ (g) was then introduced through a gas dispersion tube over 15 min, whereupon the dark green solution became a light yellow precipitate, which was stirred at ice bath temperature for an additional 20 minutes. The reaction was diluted with $CH_2Cl_2$ (56 mL), filtered over diatomaceous earth, washed with $CH_2Cl_2$ (50 mL) and the filtrate concentrated in-vacuo to yield 4.65 g as a yellow solid. Recrystallization from MeOH (15 vols) afforded 3.0 g (61.3%) as light yellow needles.

m.p. 179–181° C.; $R_f$=0.16(SiO$_2$/95:5 CH$_2$Cl$_2$:MeOH). $^1$H NMR (CDCl$_3$)δ 1.20 (t, 3H, J=7.5 Hz), 2.94 (q, 2H, J,=7.54 Hz), 3.78 (s, 3H), 4.74 (s, 2H), 5.35 (s, 2H), 5.66 (br s, 1H), 6.54 (d, 1H, J=8.0 Hz), 6.58(br s, 1H), 6.87 (d, 1H, J=8.5), 7.02–7.07 (m, 3H), 7.25–7.29 (m, 3H). $^{13}$C NMR (CDCL$_3$) δ0 14.4, 19.1, 47.0, 52.1, 65.9, 104.6, 104.8, 110.0, 117.0, 123.7, 126.1, 127.8, 129.0, 136.3, 138.3, 150.2, 151.9, 167.6, 169.7, 188.1. IR (CHCl$_3$) 3399, 1761, 1700, 16461519, 1452, 1151 cm$^{-1}$. UV (EtOH) $\lambda_{max}$ (ε)=218 (32300), 258 (126000), 333 (5500). EA Theory: C, 66.99 H, 5.62 N, 7.10; Found: C, 66.06 H, 5.64 N, 7.61 MS for C$_{22}$H$_{22}$N$_2$O$_5$: m/z=395 (m+1).

F. Preparation of ((3-(2-amino-1,2-dioxyethyl)-2-ethyl-1-(phenylmethyl)-1H-indol-4-yl)oxy)acetic acid sodium salt Compound of part F, above, was charged to a 500 ml three neck round bottom flask equipped with a mechanical stirrer and reflux condenser. The solid was slurried in EtOH (150 mL). While the slurry was stirred vigorously at room temperature, 5N NaOH (9.1 mL, 45.7 mmoles) was added. The reaction mixture was heated to reflux forming a thick white precipitate. The reaction was refluxed for 20 minutes and then cooled to room temperature. EtOH (150 mL) was added, the solid filtered on a Buchner funnel and dried in a high vac-oven at 60° C. for four hours to yield 13.67 g (89.3%) of title compound.

m.p. 296° C.; $^1$H NMR (D$_2$O)δ 1.11 (t, 3H, J=7.6 Hz), 2.96 (q, 3H, J=7.6 Hz), 4.51 (s, 2H), 5.45 (s, 2H), 6.55 (d, 1H, J=8 Hz), 6.91–7.25 (m, 8H). $^{13}$C NMR (DMSO-d$_6$) δ 14.3, 18.3, 45.9, 68.3, 103.0, 103.8, 110.1, 115.8, 123.1, 126.0, 127.3, 128.6, 137.3, 137.5, 148.1, 152.8, 169.4, 171.8, 190.0. IR (CHCl$_3$) 3028, 1649, 1411, 1276, 722 cm$^{-1}$ UV (EtOH) $\lambda_{max}$ (ε)=218 (34900), 258 (14900), 337 (5836). EA Theory: C, 62.68 H, 4.76 N, 6.96; Found: C, 62.43 H, 4.78 N, 6.69. MS for C$_{21}$H$_{19}$N$_2$O$_5$Na: m/z=381 (m-21, Na/+H).

EXAMPLE 2

((3-(aminooxoacetyl)-2-ethyl-6-methyl-1-(phenylmethyl)-1H-indol-4-yl)oxy)acetic acid sodium salt A. Preparation of 4-ethoxycarbonyl-5-methyl-1,3-cyclohexanedione sodium enolate In a three neck 250 ml flask, ethyl crotonate (32.26 g, 1.06 mol) and ethyl acetoacetate (35.45 g, 1.02 mol) were combined. Sodium ethoxide was added with stirring over two minutes. The mixture was heated to 78° C. and maintained at that temperature for one hour and 45 minutes. The reaction was allowed to cool slowly then chilled in an ice/water bath to 14° C. The reaction was filtered, rinsed twice with ethanol then dried under vacuum to recover 36.7 g (63.7%) of subtitled compound.

B. Preparation of 5-methylcyclohexanedione

In a five liter flask, 495.9 g (2.25 mol) of the compound of part A, above and a solution of potassium hydroxide (311.0 g in 1250 ml of water) were heated to reflux. After 6.5 hours, 6M HCl (1 L) was added over 25 minutes and the mixture was allowed to reflux until gas stopped evolving, approximately 1 hour. Another 100 ml of 6M HCl was added and again the reaction was allowed to reflux until no more gas evolved. A final 75 ml of 6M HCl was added and the color changed from orange to yellow. The reaction mixture was allowed to cool to 56° C. and the liquid was evaporated to yield 2728 g of material. Ethyl acetate (2.6 L) was added and the solution was transferred to a 22 L bottom outlet flask and rinsed with 500 ml of ethyl acetate followed by 500 ml MTBE and 500 ml of water. After stirring, the layers were allowed to separate. The organic layer was washed with brine (1.5 L) then dried over sodium sulfate and filtered and the organics were stripped to form a thick slurry (377 g). The slurry was filtered and rinsed with pentane (6.5 L) and the minimal amount of ethyl acetate needed to remove the yellow color. The resultant product was dried in a vacuum oven to yield 161.7 g (56.9%) of subtitled product. mp 126–128° C.

C. Preparation of ((3-(aminooxoacetyl)-2-ethyl-6-methyl-1-(phenylmethyl)-1H-indol-4-yl)oxy)acetic acid Following the procedure described in steps A–F, Example 1, above, using (160.5 g) of the compound of part B, 7.62 g (91.2%) of title compound was prepared as the sodium salt.

Elemental analysis for C$_{22}$H$_{21}$N$_2$O$_5$Na; Theory C, 63.46 H, 5.08 N, 6.72; Found C, 63.69 H, 5.16 N, 6.79.

NMR (CD3OD) 1.15 (t, 3H, J=7.2 Hz), 2.33 (s, 3H), 2.95 (q, 2H, J=7.2 Hz), 4.52 (s, 2H), 5.44 (s, 2H), 6.43 (s, 1H), 6.74 (s, 1H), 7.04 (m, 2H), 7.28 (m, 3H).

We claim:

1. A process for preparing a compound of the formula I or a pharmaceutically acceptable salt or prodrug derivative thereof

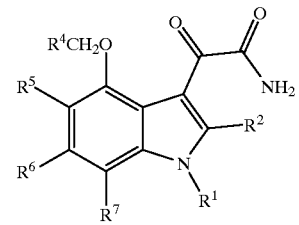

(I)

wherein:

$R^1$ is selected from the group consisting of —C$_7$–C$_{20}$ alkyl,

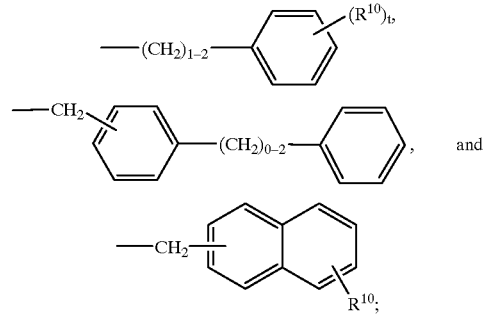

where $R^{10}$ is selected from the group consisting of halo, C$_1$–C$_{10}$ alkyl, C$_1$–C$_{10}$ alkoxy, —S—(C$_1$–C$_{10}$ alkyl) and halo (C$_1$–C$_{10}$)alkyl, and t is an integer from 0 to 5 both inclusive;

$R^2$ is selected from the group consisting of hydrogen, halo, C$_1$–C$_3$ alkyl, C$_3$–C$_4$ cycloalkyl, C$_3$–C$_4$ cycloalkenyl, —O—(C$_1$–C$_2$ alkyl), —S—(C$_1$–C$_2$ alkyl), aryl, aryloxy and HET;

$R^4$ is selected from the group consisting of —CO$_2$H, —SO$_3$H and —P(O)(OH)$_2$ or salt and prodrug derivatives thereof; and $R^5$, $R^6$ and $R^7$ are each independently selected from the group consisting of hydrogen, (C$_1$–C$_6$)alkyl, (C$_1$–C$_6$) alkoxy, halo(C$_1$–C$_6$)alkoxy, halo(C$_2$–C$_6$)alkyl, bromo, chloro, fluoro, iodo and aryl;

which process comprises the steps of:

a) halogenating a compound of formula X

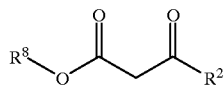  X where $R^8$ is $(C_1-C_6)$alkyl, aryl or HET; with $SO_2Cl_2$ to form a compound of formula IX

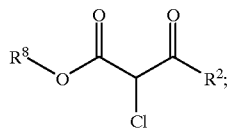  IX b) hydrolyzing and decarboxylating a compound of formula IX

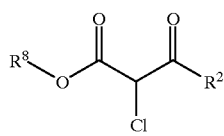  IX to form a compound of formula VIII

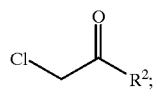  VIII c) alkylating a compound of formula VII

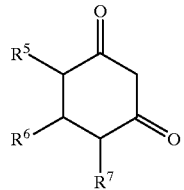  VII with a compound of formula VIII

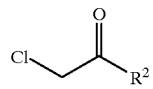  VIII to form a compound of formula VI

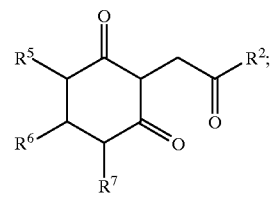  VI d) aminating and dehydrating a compound of formula VI

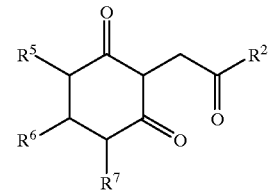  VI with an amine of the formula $R^1NH_2$ in the presence of a solvent that forms an azeotrope with water to form a compound of formula V;

e) oxidizing a compound of formula V

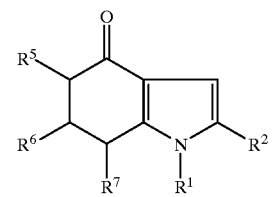  V by refluxing in a polar hydrocarbon solvent having a boiling point of at least 150° C. and a dielectric constant of at least 10 in the presence of a catalyst to form a compound of formula IV

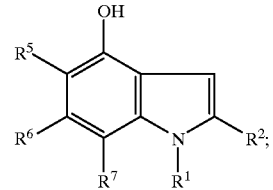  IV f) alkylating a compound of formula IV

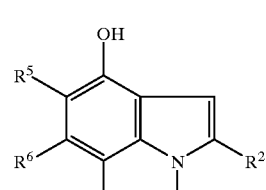  IV with an alkylating agent of the formula XCH$_2$R$^{4a}$ where X is a leaving group and R$^{4a}$ is —CO$_2$R$^{4b}$, —SO$_3$R$^{4b}$, —P(O)(OR$^{4b}$)$_2$, or —P(O)(OR$^{4b}$)H, where R$^{4b}$ is an acid protecting group to form a compound of formula III

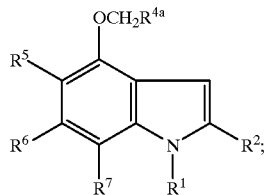

III g) reacting a compound of formula III

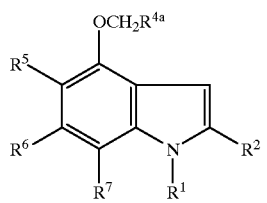

III with oxalyl chloride and ammonia to form a compound of formula II

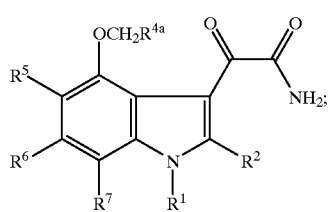

II h) optionally hydrolyzing a compound of formula II

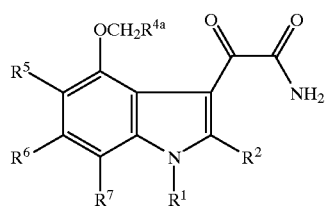

II to form a compound of formula I; and i) optionally salifying a compound of formula I.

2. The process of claim 1 where the azeotrope is toluene and the polar hydrocarbon solvent has a boiling point of from 150–250° C. and a dielectric constant of from 10–20.

3. The process of claim 1 where the azeotrope is toluene and the polar hydrocarbon solvent has a boiling point of from 150–220° C. and a dielectric constant of from 12–18.

4. The process of any one of claims 1, 2 or 3 which prepares ((3-(2-amino-1,2-dioxyethyl)-2-ethyl-1-(phenylmethyl)-1H-indol-4-yl)oxy) acetic acid.

5. A process for preparing a compound of the formula I or a pharmaceutically acceptable salt or prodrug derivative thereof

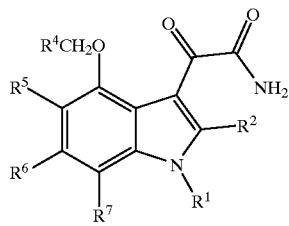

(I)

wherein:

R$^1$ is selected from the group consisting of —C$_7$–C$_{20}$ alkyl,

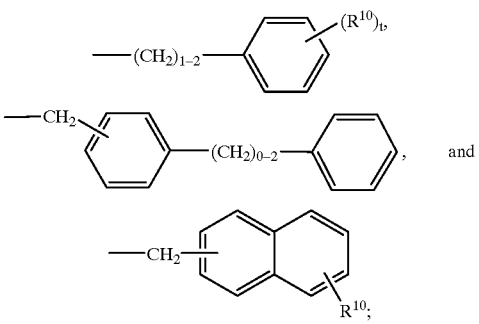

where

R$^{10}$ is selected from the group consisting of halo, C$_1$–C$_{10}$ alkyl, C$_1$–C$_{10}$ alkoxy, —S—(C$_1$–C$_{10}$ alkyl) and halo(C$_1$–C$_{10}$)alkyl, and t is an integer from 0 to 5 both inclusive;

R$^2$ is selected from the group consisting of hydrogen, halo, C$_1$–C$_3$ alkyl, C$_3$–C$_4$ cycloalkyl, C$_3$–C$_4$ cycloalkenyl, —O—(C$_1$–C$_2$ alkyl), —S—(C$_1$–C$_2$ alkyl), aryl, aryloxy and HET;

R$^4$ is selected from the group consisting of —CO$_2$H, —SO$_3$H and —P(O)(OH)$_2$ or salt and prodrug derivatives thereof; and R$^5$, R$^6$ and R$^7$ are each independently selected from the group consisting of hydrogen, (C$_1$–C$_6$)alkyl, (C$_1$–C$_6$) alkoxy, halo(C$_1$–C$_6$)alkoxy, halo(C$_2$–C$_6$)alkyl, bromo, chloro, fluoro, iodo and aryl;

which process comprises the steps of:

a) halogenating a compound of formula X

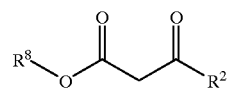

X where R$^8$ is (C$_1$–C$_6$)alkyl, aryl or HET; with SO$_2$Cl$_2$ to form a compound of formula IX

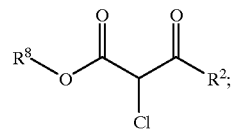

IX b) hydrolyzing and decarboxylating a compound of formula IX

IX

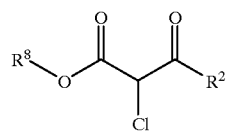

to form a compound of formula VIII

VIII

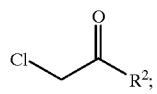

c) alkylating a compound of formula VII

VII

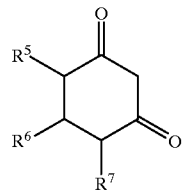

with a compound of formula VIII

VIII

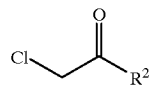

to form a compound of formula VI

VI

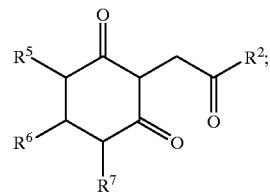

d) aminating, dehydrating and oxidizing a compound of formula VI

VI

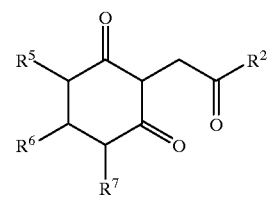

by refluxing in a polar hydrocarbon solvent having a boiling point of at least 150° C. and a dielectric constant of at least 10 in the presence of a catalyst and an amine of the formula $R^1NH_2$;

to form a compound of formula IV

IV

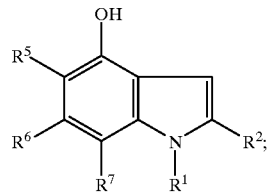

e) alkylating a compound of the formula IV

IV

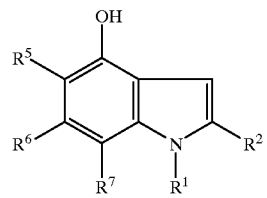

with an alkylating agent of the formula $XCH_2R^{4a}$ where X is a leaving group and $R^{4a}$ is —$CO_2R^{4b}$, —$SO_3R^{4b}$, —$P(O)(OR^{4b})_2$, or —$P(O)(OR^{4b})H$, where $R^{4b}$ is an acid protecting group to form a compound of formula III

III

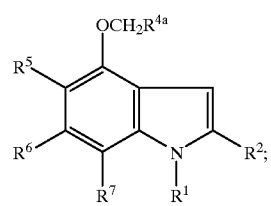

f) reacting a compound of formula III

III

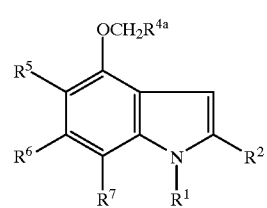

with oxalyl chloride and ammonia to form a compound of formula II

II

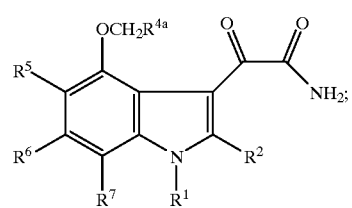

g) optionally hydrolyzing a compound of formula II $$\text{II}$$

to form a compound of formula I; and h) optionally salifying a compound of formula I.

6. A process for preparing a compound of the formula I or a pharmaceutically acceptable salt or prodrug derivative thereof $$\text{(I)}$$

wherein:

$R^1$ is selected from the group consisting of $-C_7-C_{20}$ alkyl, $-(CH_2)_{1-2}-\text{phenyl}-(R^{10})_t,$ $-CH_2-\text{phenyl}-(CH_2)_{0-2}-\text{phenyl}$, and $-CH_2-\text{naphthyl}-R^{10};$ where $R^{10}$ is selected from the group consisting of halo, $C_1-C_{10}$ alkyl, $C_1-C_{10}$ alkoxy, $-S-(C_1-C_{10}$ alkyl) and halo $(C_1-C_{10})$alkyl, and t is an integer from 0 to 5 both inclusive;

$R^2$ is selected from the group consisting of hydrogen, halo, $C_1-C_3$ alkyl, $C_3-C_4$ cycloalkyl, $C_3-C_4$ cycloalkenyl, $-O-(C_1-C_2$ alkyl), $-S-(C_1-C_2$ alkyl), aryl, aryloxy and HET;

$R_4$ is selected from the group consisting of $-CO_2H$, $-SO_3H$ and $-P(O)(OH)_2$ or salt and prodrug derivatives thereof; and $R^5$, $R^6$ and $R^7$ are each independently selected from the group consisting of hydrogen, $(C_1-C_6)$alkyl, $(C_1-C_6)$ alkoxy, halo$(C_1-C_6)$alkoxy, halo$(C_2-C_6)$alkyl, bromo, chloro, fluoro, iodo and aryl;

which process comprises the steps of:

a) aminating, dehydrating and oxidizing a compound of the formula VI $$\text{VI}$$

by refluxing in a polar hydrocarbon solvent having a boiling point of at least 150° C. and a dielectric constant of at least 10 in the presence of a catalyst and an amine of the formula $R^1NH_2$ to form a compound of formula IV $$\text{IV}$$

b) alkylating a compound of the formula IV $$\text{IV}$$

with an alkylating agent of the formula $XCH_2R^{4a}$ where X is a leaving group and $R^{4a}$ is $-CO_2R^{4b}$, $-SO_3R^{4b}$, $-P(O)(OR^{4b})_2$, or $-P(O)(OR^{4b})H$, where $R^{4b}$ is an acid protecting group, to form a compound of formula III $$\text{III}$$

c) reacting a compound of formula III $$\text{III}$$

with oxalyl chloride and ammonia to form a compound of formula II

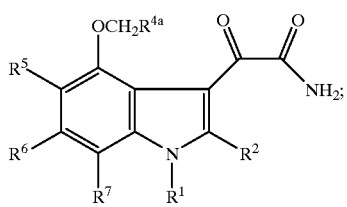

d) optionally hydrolyzing a compound of formula II

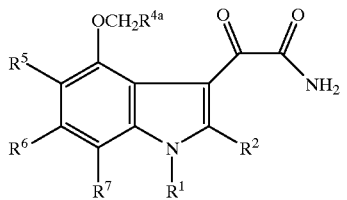

to form a compound of formula I; and e) optionally salifying a compound of formula I.

7. The process of claim 5 or 6 where the polar hydrocarbon solvent has a boiling point of from 150–250° C. and a dielectric constant of from 10–20.

8. The process of claim 5 or 6 where the polar hydrocarbon solvent has a boiling point of from 150–220° C. and a dielectric constant of from 12–18.

9. The process of any one of claims 5 to 6 which prepares ((3-(2-amino-1,2-dioxyethyl)-2-ethyl-1-(phenylmethyl)-1H-indol-4-yl)oxy) acetic acid.

10. The process of claim 7 which prepares ((3-(2-amino-1,2-dioxyethyl)-2-ethyl-1-(phenylmethyl)-1H-indol-4-yl) oxy) acetic acid.

11. The process of claim 8 which prepares ((3-(2-amino-1,2-dioxyethyl)-2-ethyl-1-(phenylmethyl)-1H-indol-4-yl) oxy) acetic acid.

12. The process of claim 1 where the polar hydrocarbon solvent is CARBITOL®.

13. The process of claim 5 where the polar hydrocarbon solvent is CARBITOL®.

* * * * *